United States Patent [19]

Nomura

[11] Patent Number: 5,160,332
[45] Date of Patent: Nov. 3, 1992

[54] BLOOD RESERVOIR

[75] Inventor: Osamu Nomura, Fuji, Japan

[73] Assignee: Terumo Kabushiki Kaisha, Tokyo, Japan

[21] Appl. No.: 457,785

[22] PCT Filed: Jul. 6, 1988

[86] PCT No.: PCT/JP88/00680
§ 371 Date: Jan. 2, 1990
§ 102(e) Date: Jan. 2, 1990

[87] PCT Pub. No.: WO89/00055
PCT Pub. Date: Dec. 1, 1989

[30] Foreign Application Priority Data

Jul. 7, 1987 [JP] Japan .................. 62-167769

[51] Int. Cl.⁵ .................................... A61M 1/00
[52] U.S. Cl. ............................ 604/405; 604/4;
604/122; 604/406; 210/436; 422/44; 422/48
[58] Field of Search ....................... 604/4–6,
604/405, 406, 408–411, 122; 477/44, 48;
210/131, 188, 436

[56] References Cited

U.S. PATENT DOCUMENTS

| | | | |
|---|---|---|---|
| 4,423,438 | 5/1990 | Vasconcellos et al. | 604/4 |
| 4,493,705 | 1/1985 | Gordon et al. | 604/122 |
| 4,620,965 | 11/1986 | Fukusawa et al. | |
| 4,734,269 | 3/1988 | Clarke et al. | 604/405 X |
| 4,806,135 | 2/1989 | Siposs | 210/456 X |
| 4,976,708 | 12/1990 | Oshiyama | 604/4 X |

FOREIGN PATENT DOCUMENTS

50-30958 10/1975 Japan .
55-180536 12/1980 Japan .
59-57661 4/1984 Japan .
59-196234 12/1984 Japan .
61-44031 10/1986 Japan .
62-5356 1/1987 Japan .
62-258671 11/1987 Japan .

Primary Examiner—Robert A. Hafer
Assistant Examiner—Kerry Owen
Attorney, Agent, or Firm—Frishauf, Holtz, Goodman & Woodward

[57] ABSTRACT

A blood reservoir serves to suppress generation of air bubbles in blood in an extracorporeal blood circulation circuit. The blood reservoir includes a blood storage chamber for temporarily storing the blood, the blood storage chamber having blood inlet and outlet ports, and a fluid-permeable blood spouting inhibitor disposed over the blood inlet port. Since the blood flows into the blood storage chamber through the blood spouting inhibitor, the blood is prevented from being spouted into the blood reservoir, so that air bubbles are prevented from being generated in the blood.

11 Claims, 5 Drawing Sheets

BLOOD RESERVOIR

TECHNICAL FIELD

The present invention relates to a blood reservoir, and more particularly to a blood reservoir for use with an artificial lung, the blood reservoir having a fluid-permeable blood spouting inhibitor disposed over blood inlet ports for uniforming the flow of blood in the blood reservoir thereby to avoid the danger of mixing air bubbles in the blood.

BACKGROUND ART

When a surgical operation is effected on the chest of a patient, an extracorporeal blood circulation circuit including an artificial lung is used in recent years in bypassing relation to the lung of the patient, and carbon dioxide is removed from the blood of the patient and fresh oxygen is added to the blood by the artificial lung.

The extracorporeal blood circulation circuit includes a blood reservoir for temporarily storing the blood s that air bubbles produced during the circulation of the blood will be removed from the blood, or for supplying stored blood to make up for a reduction in the rate of circulation of the blood. Blood reservoirs now in use in the art are roughly classified into a soft bag reservoir which is made of a soft material, and a hard shell reservoir which is made of a hard material. The soft bag reservoir is advantageous in that it has no blood-air interface, but disadvantageous in that it cannot hold a large amount of blood and cannot give an exact indication of how much blood is stored therein.

The hard shell reservoir can store a large amount of blood and allows the user to know the exact amount of blood stored therein. Other advantages of the hard shell container are that it can easily be united with an artificial lung, thus permitting an extracorporeal blood circulation circuit to be simplified, and also the blood can easily be debubblized when the extracorporeal blood circulation circuit is set up and primed. Japanese Laid-Open Patent Publication No. 59(1984)-57661, for example, proposes a hard shell blood reservoir combined with an artificial lung in view of the above functions and advantages.

It is very important that a hard shell blood reservoir be capable of reliably removing air bubbles which have been introduced into the blood through a blood extracting tube. If the blood containing air bubbles were returned to the patient, then the patient would suffer from the danger of embolism. The hard shell blood reservoir therefore has a debubblizer for removing air bubbles from the stored blood.

Figure 1:
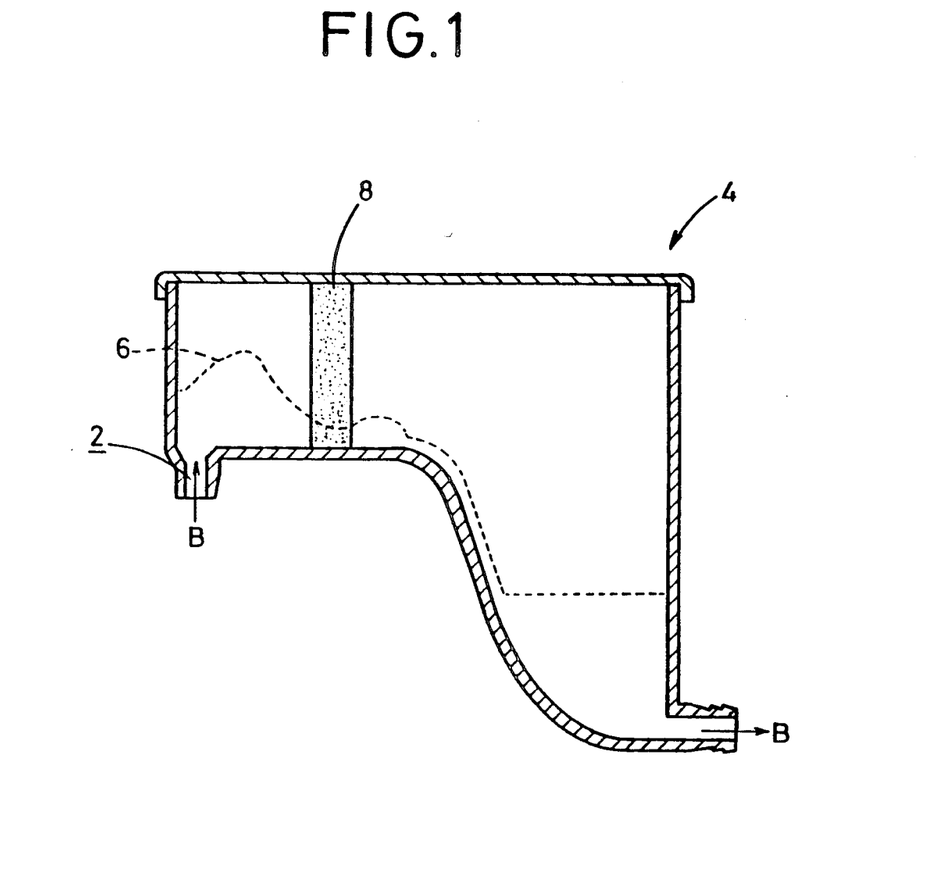
FIG. 1 is a schematic elevational view of a blood reservoir as a comparative example.

The applicant has devised a hard shell blood reservoir having a blood inlet port opening at a bottom thereof, as shown in FIG. 1 of the accompanying drawings. If a large amount of blood G flows from the blood inlet port 2 into the blood reservoir 4, the blood tends to be forcibly spouted as indicated by the dotted line 6 in FIG. 1. Therefore, the blood in the blood reservoir 4 is liable to be ununiform in flow, or air bubbles is apt to be trapped in the blood. The blood reservoir 4 has a blood debubblizer 8 for removing air bubbles from the blood. If the flow of the blood B becomes ununiform, then the debubblizing capability of debubblizer 8 is lowered, and also new air bubbles are produced by the ununiform blood flow.

One solution to the above problems due to the spouting of the blood B from the blood inlet port 2 into the blood reservoir 4 would be to provide a region for allowing the blood B to stay therein in the vicinity of the blood inlet port 2. However, if such a region is large enough to uniformize the blood flow caused by the spouted blood B, then the amount of blood stored in the blood reservoir 4 is increased, and hence the priming volume of the extracorporeal blood circulation circuit, with the result that the burden on the patent is also increased.

DISCLOSURE OF THE INVENTION

In view of the aforesaid drawbacks of the conventional blood reservoirs, it is an object of the present invention to provide a blood reservoir which can prevent blood introduced from blood inlet ports from being spouted and uniformize the flow of blood in the blood reservoir without involving an increase in the amount of stored blood, so that the danger of mixing air bubbles in the blood will be minimized.

To achieve the above object, there is provided in accordance with the present invention a blood reservoir comprising a blood inlet port, a blood storage chamber communicating with the blood inlet port, and a blood outlet port defined in a lower portion of the blood storage chamber, characterized by a fluid-permeable blood spouting inhibitor disposed at the blood inlet port.

The blood inlet port opens vertically upwardly.

The fluid-permeable blood spouting inhibitor is disposed in substantially covering relation to the blood inlet port.

The fluid-permeable blood spouting inhibitor comprises a mesh structure.

The mesh structure has a mesh number ranging from 10 to 40.

The mesh structure substantially covers the blood inlet port with only one end of the mesh structure being fixed.

The blood reservoir further includes a blood inlet chamber extending from the blood inlet port to the blood storage chamber, and a blood debubblizer disposed transversely across a blood passage defined by the blood inlet chamber.

BEST MODE FOR CARRYING OUT THE INVENTION

A preferred embodiment of a blood reservoir according to the present invention will be described in detail with reference to the accompanying drawings.

Figure 2:
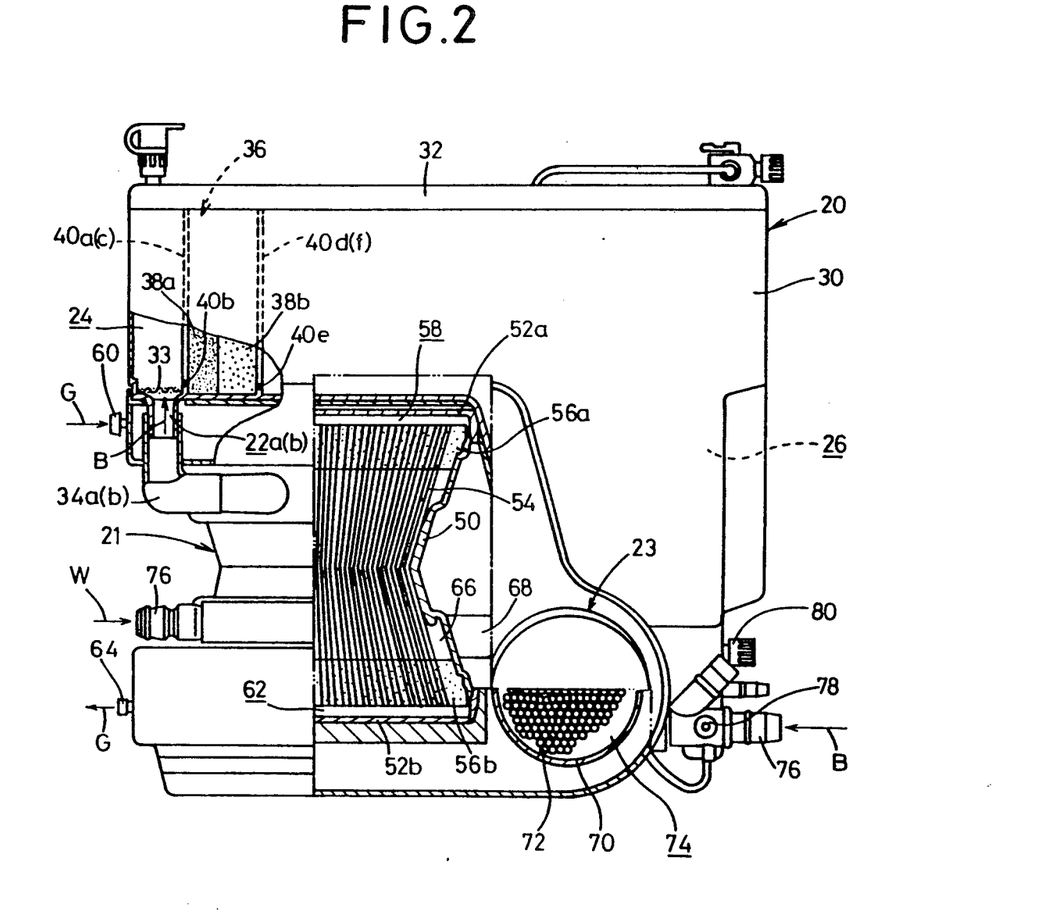
FIG. 2 is a side elevational view, partly in cross section, of an artificial lung apparatus incorporating a blood reservoir according to the present invention.

FIG. 2 shows a blood reservoir 20 according to the present invention which is combined with an artificial lung 21 for exchanging oxygen and carbon dioxide in blood B and a heat exchanger 28 for keeping the blood B at a predetermined temperature.

The blood reservoir 20 will first be described with reference to FIGS. 3 and 4.

The blood reservoir 20 is a blood reservoir of the hard shell type for use in an artificial lung circuit. As shown in FIG. 3, the blood reservoir 20 has a pair of blood inlet ports 22a, 22b, a blood inlet chamber 24 communicating with the blood inlet ports 22a, 22b and having a bottom which is substantially at the same level as the blood inlet ports 22a, 22b, a blood storage chamber 26 communicating with the blood inlet chamber 24 and having a bottom extending progressively downwardly from the blood inlet chamber 24, and a blood outlet port 28 defined in the lower end of the blood storage chamber 26. The blood reservoir 20 comprises a container housing 30 of a hard material such as hard polyvinyl chloride, polystyrene, polycarbonate, or the like. The container housing 30 has an upper opening closed by a cover 32. The container housing 30 should preferably be transparent so as to allow the user to visually observe the blood B stored in the container casing 2.

A fluid-permeable blood spouting inhibitor or blood flow stabilizer 33 is disposed over the blood inlet ports 22a, 22b. The blood inlet ports 22a, 22b are connected to blood outlet tubes 34a, 34b (see FIG. 2) from the artificial lung 21. The blood spouting inhibitor 33 serves to lessen or stabilize the flow of the blood B introduced from the blood inlet ports 22a, 22b into the blood reservoir 20. The blood spouting inhibitor 33 comprises a mesh of woven fiber members and is disposed over the blood inlet ports 22a, 22b with only one side 33a near the blood storage chamber 24 being fixed to the bottom of the blood inlet chamber 24 near the blood inlet ports 22a, 22b by adhesive bonding, thermal fusion, or the like.

The blood inlet chamber 24 communicating with the blood inlet ports 22a, 22b defines a blood passage extending from the blood inlet ports 22a, 22b through the blood spouting inhibitor 33 to the blood storage chamber 26. The blood inlet chamber 24 is higher in position than the blood storage chamber 26, and has a bottom which is substantially at the same level as the blood inlet ports 22a, 22b, as described above. The bottom of the blood inlet chamber 24 may be flat or semicylindrical in shape. However, the flat bottom is preferable since a blood debubblizer (described later) can easily be placed thereon. The blood storage chamber 26 communicating with the blood inlet chamber 24 serves to store the blood B which has flowed into the blood reservoir 20. The bottom of the blood storage chamber 26 extends progressively downwardly from the blood inlet chamber 24. The blood B which is temporarily stored in the blood reservoir 20 is discharged out from the blood outlet port 28 defined in the lower end of the blood storage chamber 26.

The blood reservoir 20 also has a blood debubblizer 36 disposed in the housing 30 and extending transversely fully in and across the blood passage defined by the blood inlet chamber 24. The debubblizer 36 serves to remove air bubbles from the blood B which has flowed into the blood inlet chamber 24 so that the blood B free of air bubbles can be delivered into the blood storage chamber 26. The debubblizer 36 is generally in the form of of foamed bodies which are of a hydrophobic nature to allow air bubbles in the blood to grow and be removed. The foamed body is of a three-dimensional mesh structure. In the illustrated embodiment, the debubblizer 36 is composed of a foamed body 38a of a larger mesh number and a foamed body 38b of a smaller mesh number, the foamed bodies 38a, 38b are arranged size by size. The foamed body 38a is positioned closer to the blood inlet ports 22a, 22b, whereas the foamed body 38b is positioned closer to the blood storage chamber 26. The mesh number referred to above represents the number of interstices or openings occurring per length of 25.4 mm (1 inch), and is originally an indication of the size of openings of a screen or sieve.

The debubblizer 36 is held in intimate contact with the bottom of the blood inlet chamber 24 and extends across the full width of the blood passage so that the incoming blood B will be in full contact with the debubblizer 36. The debubblizer 36 is also held in intimate contact with the side walls of the housing 30. The upper end of the debubblizer 36 is preferably held in intimate contact with the cover 32 mounted on the top of the housing 30 in order to prevent the debubblizer 36 from being moved by the blood flow or to prevent the blood B from flowing out beyond the upper end of the debubblizer 36. The housing 30 has ridges 40a through 40f projecting from the inner side and bottom surfaces thereof on both lateral sides of the debubblizer 36.

The artificial lung 21 coupled to the blood reservoir 20 comprises a housing 50 and attachment covers 52a, 52b closing the upper and lower ends, respectively, of the housing 50. The housing 50 accommodates therein a number of hollow fiber membranes 54 which are vertically disposed in spaced relation to each other. The hollow fiber membranes 54 have opposite open ends held in the housing 50 by partitions 56a, 56b in a fluidtight manner with the open ends remaining open. The attachment cover 52a, the housing 50, and the partition 56a jointly define a gas inlet space 58 communicating with the hollow spaces in the hollow fiber membranes 54 and connected to a gas inlet port 60. The other attachment cover 52b, the housing 50, and the partition 56b jointly define a gas outlet space 62 communicating with the hollow spaces in the hollow fiber membranes 54 and connected to a gas outlet port 64. The inner wall surface of the housing 50, the partitions 56a, 56b, and the outer wall surfaces of the hollow fiber membranes 54 jointly define a blood chamber 66 connected to a blood inlet tube 68 communicating with the heat exchanger 23 and the blood outlet tubes 34a, 34b which communicate with the blood reservoir 20.

The blood outlet tubes 34a, 34b of the artificial lung 21 are joined in a fluidtight manner to the blood inlet ports 22a, 22b of the blood reservoir 20. The blood outlet tubes 34a, 34b and the blood inlet ports 22a, 22b may be joined by threaded interfitting engagement, tapered interfitting engagement, fitting engagement through an O-ring, ultrasonic or high-frequency bonding, or adhesive bonding.

The artificial lung 21 is of the type which delivers a gas G containing oxygen such as air into the hollow fiber membranes 54 and allows the blood B to flow outside of the hollow fiber membranes 54 for a gaseous exchange between the gas G and the blood G. Alternatively, the artificial lung 21 may be of the type which delivers the blood B into the hollow fiber membranes 54 and the gas G containing oxygen around the hollow fiber membranes 54 for a gaseous exchange between the gas G and the blood B, or of the type which includes flat membranes for a gaseous exchange. Preferably, the artificial lung 21 should be of the type which passes the blood B around the hollow fiber membranes 54 as described above in this embodiment. With the artificial lung 21 of this type being employed, since any pressure loss across the artificial lung 21 is small, a blood circulation circuit incorporating the blood reservoir 20 is not required to have a blood delivery pump in front of the artificial lung 21, but the blood B can be fed by gravity from the patient to the artificial lung 21 and the blood reservoir 20.

The heat exchanger 23 is coupled to the blood inlet tube 68 of the artificial lung 21. The heat exchanger 23 has a number of heat exchanging tubes 72 disposed in a casing 70 in spaced relation to each other and extending in the longitudinal direction of the casing 70. The opposite open ends of the heat exchanging tubes 72 are held on side walls of the casing 70 by partitions (not shown) in a fluidtight manner, with the open ends of the tubes 72 remaining open. The partitions, the side walls of the casing 70, and the outer wall surfaces of the heat exchanging tubes 72 jointly define a space 74 which communicates with a blood inlet port 76 and the blood inlet tube 68 of the artificial lung 21. The inner spaces in the heat exchanging tubes 72, which are isolated from the space 74 in a fluidtight manner, communicate with a water inlet port 77 communicating with the exterior of one of the partitions of the casing 70 and a water outlet port (not shown) communicating with the exterior of the other partition of the casing 70. Warm or cold water W is supplied from the water inlet port 77 into the heat exchanging tubes 72, and warms or cools the blood B held in contact with the heat exchanging tubes 72. The heat exchanger 23 may be of the type in which the blood B is passed through the heat exchanging tubes 72 and a cooling or warming medium is passed around the heat exchanging tubes 72. The heat exchanger 23 and the blood reservoir 20 further have ports 78, 80, respectively, for the insertion of temperature sensor probes.

The blood reservoir of the above embodiment is basically constructed as described above. Operation and advantages of the blood reservoir will be described below.

The blood reservoir 20, the artificial lung 21, and the heat exchanger 23 which are combined together serve as an artificial lung apparatus. The blood B is introduced from the blood inlet port 76 into the casing 70 of the heat exchanger 23, and warmed or cooled by the water W flowing through the heat exchanging tubes 72 while the blood B is flowing toward the blood inlet tube 68 of the artificial lung 21.

Then, the blood B flows from the blood inlet tube 68 into the housing 50 of the artificial lung 21. During passage through the blood chamber 66, a gaseous exchange is effected between the blood B and the gas G containing oxygen which flows through the hollow fiber membranes 54, thereby removing excessive carbon dioxide from the blood B and adding oxygen to the blood B. The blood B to which oxygen is added flows out of the artificial lung 21 from the blood outlet tubes 34a, 34b and flows into the blood reservoir 20 through the blood inlet ports 22a, 22b and the blood spouting inhibitor 33.

Figure 3:
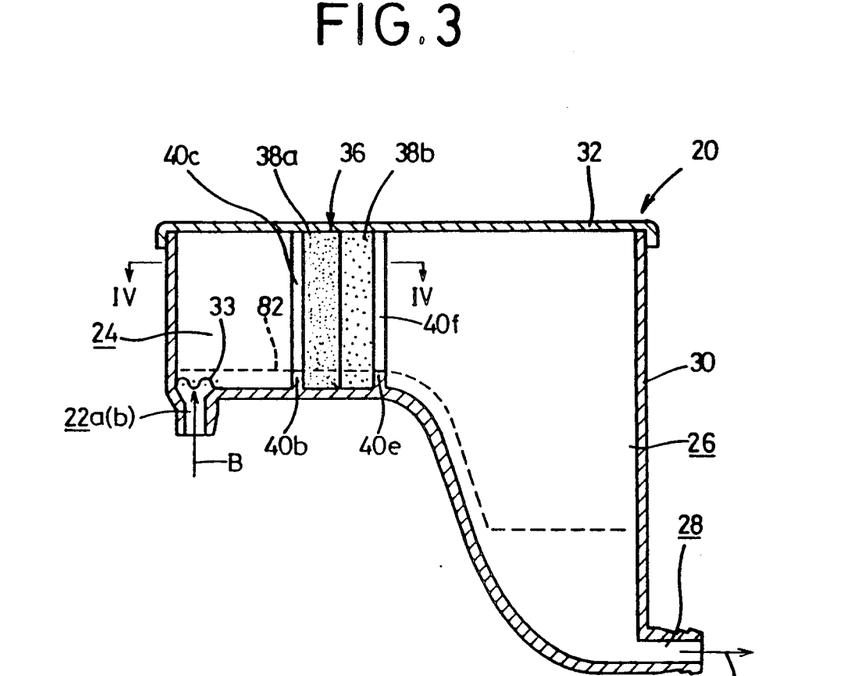
FIG. 3 is a vertical cross-sectional view of the blood reservoir of the invention.

Since the blood B flowing into the blood reservoir 20 is reduced in speed when it passes through the fluid-permeable blood spouting inhibitor 33, the blood B flowing from the blood inlet ports 22a, 22b does not spout as indicated by the dotted line 82 in FIG. 3, and the danger of producing air bubbles in the blood due to localized blood flows is minimized.

The blood spouting inhibitor 33 is not limited to any size and configuration insofar as it can effectively interfere with the blood B from the blood inlet ports 22a, 22b. However, it is preferable that the blood spouting inhibitor 33 substantially cover the blood inlet ports 22a, 22b. The blood spouting inhibitor 33 is also not limited to any structure insofar as it is permeable to fluids. However, it is preferable that the blood spouting inhibitor 33 be of a mesh structure capable of effectively acting on the blood B and developing a small pressure loss due to contact with the blood B. If the blood spouting inhibitor 33 is a mesh, then the mesh number thereof should preferably range from 10 to 40, particularly from 15 to 35. If the mesh size of the blood spouting inhibitor 33 were smaller than 10, it would not sufficiently effective to suppress the generation of air bubbles upon an increase in the amount of blood flowing therethrough. If the mesh number were in excess of 40, air bubbles flowing from the blood inlet ports 22a, 22b and attached to the mesh would tend to flow into the blood reservoir 20 after elapse of a certain period of time. The blood spouting inhibitor 33 should preferably be made of a material that has a less tendency to activate the components of the blood upon contact therewith. For example, such a material may be polyvinyl chloride, polyethylene, polypropylene, polyester, polycarbonate, or the like.

Figure 4:
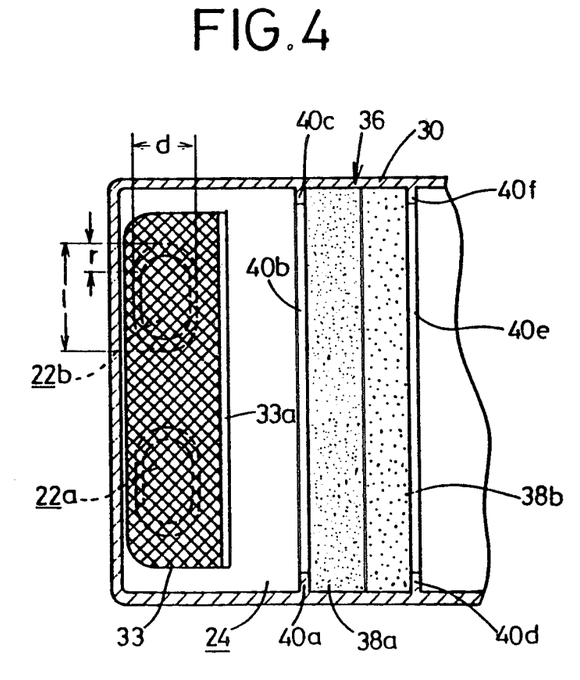
FIG. 4 is a cross-sectional view taken along line IV—IV of FIG. 3.

Most preferably, the blood spouting inhibitor 33 should be arranged such that, as shown in FIGS. 3 and 4, the blood spouting inhibitor 33 of a mesh structure is positioned in substantially covering relation to the blood inlet ports 22a, 22b with only the side 33a thereof being fixed. If the opposite ends of the blood spouting inhibitor 33 were fixed, then air bubbles introduced from the blood inlet ports 22a, 22b would tend to be broken up by the blood spouting inhibitor 33. If the mesh structure is of a small mesh size, it is apt to develop an increased pressure loss. With only the side 33a of the blood spouting inhibitor 33 being fixed, when air bubbles flow in from the blood inlet ports 22a, 22b, the mesh structure tend to flex for thereby allowing air bubbles to pass without breaking them up and also preventing the pressure loss from being increased.

The blood B introduced from the blood inlet ports 22a, 22b now reaches the debubblizer 36 in the blood inlet chamber 24. Air bubbles contained in the blood B contact the cells of the foamed bodies 38a, 38b of the debubblizer 36 and are combined into larger air bubbles, which are moved from the blood B into an upper space in the blood reservoir 20 and are reliably removed. Inasmuch as the two foamed bodies 38a, 38b have different mesh sizes which become smaller in the direction in which the blood B flows, the pressure loss across the debubblizer 36 is not increased, and the air bubbles in the blood B are brought into sufficient contact with the cells of the foamed bodies 38a, 38b, with the result that the blood B is effectively debubblized.

The blood B from which air bubbles have been removed by the debubblizer 36 flows from the blood inlet chamber 24 into the blood storage chamber 26. After the blood B has temporarily been stored in the blood storage chamber 26, it is delivered to the patient's body from the blood outlet port 38 in the lower end of the blood storage chamber 26.

An experiment conducted on the blood reservoir of the present invention will be described below.

There was employed a blood reservoir 20 including a housing 30 having a storage capacity of 4 l, with each of blood inlet ports 22a, 22b being of an elliptical shape having a length (l) of 42 mm, a width (d) of 12.2 mm, and an end radius (r) of 6.1 mm, as shown in FIG. 4. The blood inlet chamber 24 had a flat surface up to the front edge of the debubblizer 36, the flat surface having a length of 30 mm and a width of 150 mm. The debubblizer 36 was disposed in the blood inlet chamber 24 across the blood passage thereof and composed of a foamed body 38a (having a thickness of 15 mm) made of a polyurethane foam having a mesh number of 13, the foamed body 38a being positioned closer to the blood inlet ports 22a, 22b, and a foamed body 38b (having a thickness of 15 mm) made of a polyurethane foam having a mesh number of 8, the foamed body 38b being held closely against the foamed body 38a and positioned closer to the blood storage chamber 26. Nets of polypropylene having various mesh number shown in Table 1, below, were disposed as the blood spouting inhibitors 33 according to Inventive Examples 1 through 5 over the blood inlet ports 22a, 22b, with the side 33a being fixed, as shown in FIG. 4.

Figure 5:
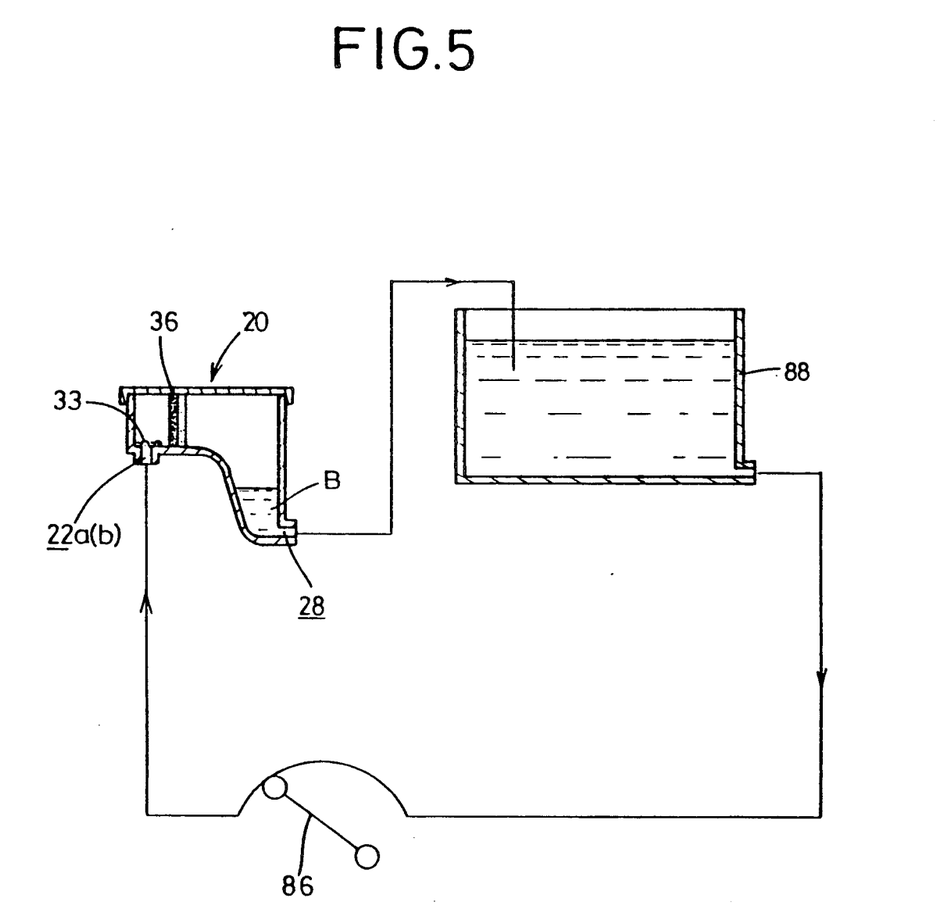
FIG. 5 is a diagram of a blood circuit employed in a blood circulation experiment conducted on the blood reservoir according to the present invention.

An experimental blood circuit was constructed of the blood reservoir 20 and a blood storage tank 88 having a storage capacity of 20 l and connected to the blood reservoir 20 by a roller pump 86. Using the experimental blood circuit and employing the blood spouting inhibitors 33 of different mesh number, a blood circulation experiment was carried out at blood flow rates of 4 l/min. and 6 l/min. to determine how the blood B was spouted from the blood inlet ports 22a, 22b. The results of the experiment are shown in Table 1 and FIG. 6.

A comparative blood circulation experiment was also conducted using the same blood reservoir as the blood reservoirs 20 according to inventive examples 1 through 5 in Table 1 except that no blood spouting inhibitor 33 is disposed over the blood inlet ports 22a, 22b, and also using the same experimental blood circuit as described above, and it was determined how the blood B was spouted from the blood inlet ports 22a, 22b.

TABLE 1

| | | Spout height (mm) | |
| --- | --- | --- | --- |
| | Mesh size | Flow rate (4 l/mm) | Flow rate (6 l/mm) |
| Comparative Example | — | 23 | 32 |
| Inventive Example 1 | 5 | 18 | 27 |
| Inventive Example 2 | 7 | 17 | 25 |
| Inventive Example 3 | 11.5 | 12 | 17 |
| Inventive Example 4 | 14.5 | 10 | 16 |
| Inventive Example 5 | 33.5 | 9 | 12 |

Figure 6:
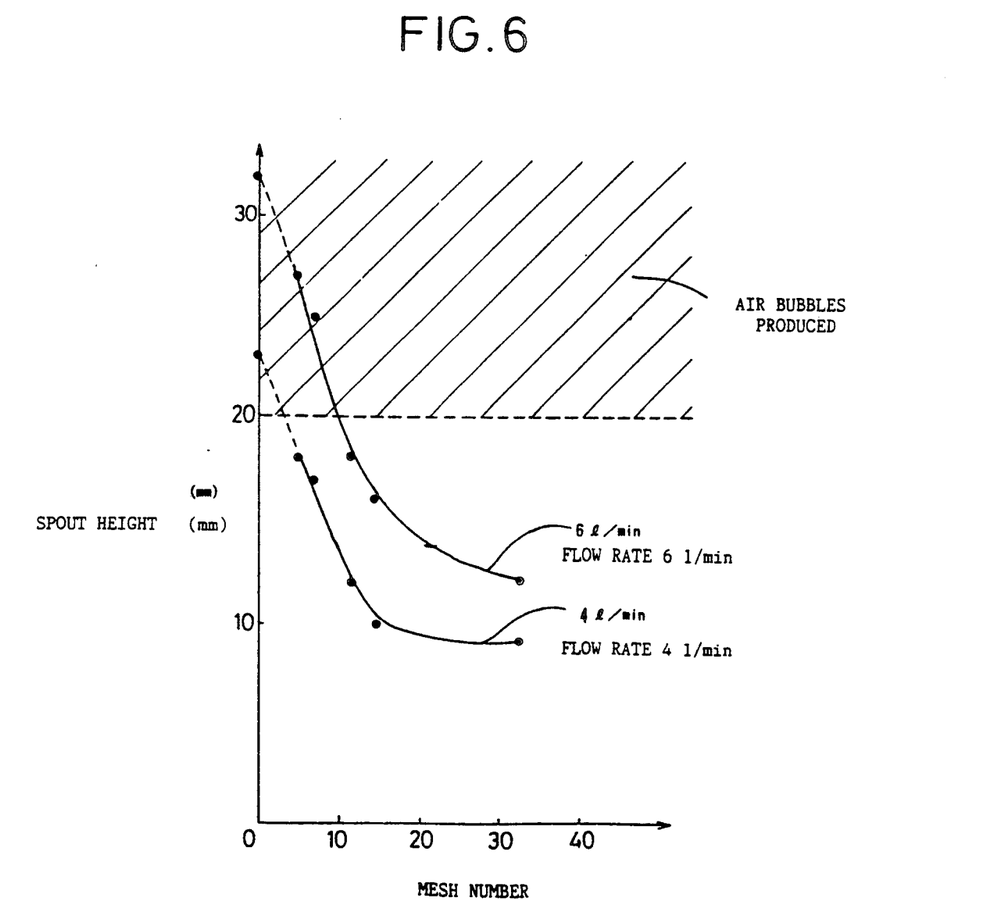
FIG. 6 is a diagram showing the relationship between the mesh size of a blood spouting inhibitor employed in the blood reservoir of the invention and the height of a blood spout.

The height of the spout of the blood B from the blood inlet ports 22a, 22b in the blood reservoirs 20 which have the blood spouting inhibitors 33 (according to Inventive Examples 1 through 5) was apparently lower than that in the blood reservoir which has no blood spouting inhibitor 33 (according to Comparative Example). Moreover, the spout height was progressively lower as the mesh size of the blood spouting inhibitor 33 is increased (i.e., the size of mesh openings is reduced). When the spout height exceeded about 20 mm, air bubbles were produced.

INDUSTRIAL APPLICABILITY

With the present invention, as described above, the blood reservoir includes a blood storage chamber having blood inlet ports and a blood outlet port, and a fluid-permeable blood spouting inhibitor disposed over the blood inlet ports. Since blood flowing in from the blood inlet ports is retarded by the blood spouting inhibitor, the blood does not spout into the blood reservoir, and hence the danger of generation of air bubbles due to located blood flows is minimized. As a result, it is possible to achieve safer extracorporeal circulation of blood when the blood reservoir is incorporated in an extracorporeal blood circulation circuit.

The fluid-permeable blood spouting inhibitor is more effective in preventing the incoming blood from being spouted if the blood spouting inhibitor substantially covers the blood inlet ports. If the fluid-permeable blood spouting inhibitor is of a mesh structure, particularly a mesh structure having a mesh size ranging from 10 to 40, and is positioned in covering relation to the blood inlet ports with only one end thereof being fixed, then any pressure loss across the blood spouting inhibitor is almost eliminated, but the blood spouting inhibitor can well prevent the blood from being spouted.

Although a certain preferred embodiment has been shown and described, it should be understood that many changes and modifications may be made therein without departing from the scope of the appended claims.

I claim:

1. A blood reservoir comprising:
   a blood inlet port;
   a blood storage chamber communicating with the blood inlet port;
   a blood outlet port defined in a lower portion of the blood storage chamber; and
   a fluid-permeable blood spouting inhibitor comprising a mesh structure having respective side edges disposed over said blood inlet port in substantially covering relation thereto, with only one of said side edges of the mesh structure being fixed, said mesh structure being flexible upwardly with respect to said blood inlet port for allowing air bubbles in the blood to bypass said mesh structure without breaking apart while allowing blood from said blood inlet port to flow through said mesh structure.

2. A blood reservoir according to claim 1, wherein said blood inlet port opens vertically upwardly.

3. A blood reservoir according to claim 1 or 2, wherein said mesh structure has a mesh number ranging from 10 to 40.

4. A blood reservoir according to claim 1 or claim 2, further comprising:
   a blood inlet chamber extending from said blood inlet port to said blood storage chamber; and
   a blood debubblizer disposed transversely across a blood passage defined by said blood inlet chamber.

5. A blood reservoir comprising:
   a blood storage chamber including: a substantially rigid container having side walls; a bottom surface; a blood inlet section; and a blood storage section;
   at least one blood inlet port defined in the bottom surface of said blood storage chamber in said blood inlet section;

a blood outlet port defined in a lower portion of said blood storage chamber in said blood storage section; and a fluid permeable blood spouting inhibitor comprising:

a substantially flat mesh structure disposed on a bottom surface of said blood inlet section over said at least one blood inlet port to substantially cover said at least one inlet port; and only a portion of said mesh structure being fixedly attached to said bottom surface of said blood inlet section.

6. A blood reservoir according to claim 5, wherein:

said mesh structure comprises a substantially rectangular mesh member having respective side edges; and only one of said respective side edges of said substantially flat, substantially rectangular, mesh number is fixedly attached to said bottom surface.

7. A blood reservoir according to claim 5, wherein said mesh structure has a mesh number ranging from 10 to 40.

8. A blood reservoir according to claim 5, further comprising a blood debubblizer disposed transversely across a blood passage defined between said blood inlet section and said blood storage section.

9. A method for smoothing the flow of blood through a blood reservoir having at least one blood inlet port and a blood outlet port defined in a lower portion of the blood reservoir, comprising:

flowing blood, including air bubbles therein, through said at least one blood inlet port;

inhibiting blood spouting, as blood flows through said at least one blood inlet port, by positioning a fluid permeable spout inhibitor over said at least one blood inlet port, said spout inhibitor comprising a flexible mesh having an edge portion;

attaching at least a portion of said edge portion of said mesh to cover said at least one blood inlet port, whereby said fluid permeable spout inhibitor is flexible upwardly with respect to said blood inlet port; and flexing said fluid permeable spout inhibitor upwardly with respect to said blood inlet port, to permit at least some of the air bubbles in the blood flowing in said at least one blood inlet port to bypass said fluid permeable spout inhibitor substantially without breaking apart while simultaneously permitting blood from said at least one blood inlet port to flow through said fluid permeable spout inhibitor.

10. A method according to claim 9, further comprising:

providing debubblizer means between the fluid permeable spout inhibitor and the blood outlet port for removing air bubbles in the blood supplied by said at least one blood inlet port including the air bubbles which bypassed said fluid permeable spout inhibitor.

11. A method according to claim 9, wherein:

said fluid permeable spout inhibitor comprises a flexible mesh having a mesh number of at least 10 and not more than 40.

* * * * *

UNITED STATES PATENT AND TRADEMARK OFFICE
CERTIFICATE OF CORRECTION

PATENT NO. : 5,160,332
DATED : November 3, 1992
INVENTOR(S) : NOMURA, Osamu

It is certified that error appears in the above-indentified patent and that said Letters Patent is hereby corrected as shown below:

Column 1, line 9, change "unforming" to read
--making uniform (smoothing)--.

Column 1, line 21, change "s" to read --so--.

Column 1, line 56, change "G" to read --B--.

Column 1, line 60, change "bubbles is" to read
--bubbles are--.

Column 4, line 8, change "size by size" to read
--side by side--.

Column 6, line 18, after "would not", insert --be--.

Signed and Sealed this

Fourteenth Day of December, 1993

Attest:

BRUCE LEHMAN

*Attesting Officer*  *Commissioner of Patents and Trademarks*